US007550163B2

(12) United States Patent
Palpu et al.

(10) Patent No.: US 7,550,163 B2
(45) Date of Patent: Jun. 23, 2009

(54) HERBAL SOFT DRINK

(75) Inventors: Pushpangadan Palpu, Lucknow (IN);
Shanta Mehrotra, Lucknow (IN); Ajay Kumar Singh Rawat, Lucknow (IN);
Sayyada Khatoon, Lucknow (IN);
Sanjeev Kumar Ojha, Lucknow (IN);
Subha Rastogi, Lucknow (IN);
Manjoosha Srivastava, Lucknow (IN);
Prahlad Kishore Seth, Lucknow (IN);
Ashok Kumar Agarwal, Lucknow (IN);
Poonam Kakkar, Lucknow (IN);
Mohini Anand, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/539,427

(22) PCT Filed: Dec. 20, 2002

(86) PCT No.: PCT/IB02/05558

§ 371 (c)(1),
(2), (4) Date: Jan. 17, 2006

(87) PCT Pub. No.: WO2004/056382

PCT Pub. Date: Jul. 8, 2004

(65) Prior Publication Data

US 2006/0147554 A1 Jul. 6, 2006

(51) Int. Cl.
*A61K 36/87* (2006.01)
*A61K 36/00* (2006.01)

(52) U.S. Cl. .................... 424/766; 424/725

(58) Field of Classification Search .......... None
See application file for complete search history.

(56) References Cited

U.S. PATENT DOCUMENTS

2002/0025349 A1 * 2/2002 Brindavanam et al. ...... 424/757
2003/0129258 A1 * 7/2003 Pushpangadan et al. ..... 424/725

FOREIGN PATENT DOCUMENTS

| DE | 4012000 | * | 10/1990 |
| GB | 2 314 270 A | | 12/1997 |
| JP | 58179476 | * | 10/1983 |
| JP | 01181782 | * | 7/1989 |
| RU | 588236 | * | 2/1978 |
| RU | 2065280 | * | 8/1996 |
| RU | 2108050 | * | 4/1998 |
| SU | 631532 | * | 11/1978 |
| WO | WO 98 05346 A | | 2/1998 |
| WO | WO 98/05346 A1 | | 2/1998 |
| WO | WO 03 017784 A | | 3/2003 |
| WO | WO 03/017784 A1 | | 3/2003 |

OTHER PUBLICATIONS

Derwent English Abstract of German Patent Application DE-401200.*
Singh et al., "Evaluation of Geriforte, an Herbal Geriatric Tonic, On Antioxidant Defense System in Wistar Rats," 1994, Annals of the New York Academy of Sciences, 717, June , p. 170.*
Himalayan Herbal Healthcare webpage, "Geriforte," Internet Archive Wayback Machine, Jun. 2002, retrieved Feb. 20, 2008, http://web.archive.org/web/20020603201320/http://www.himalayahealthcare.com/products/geriforte.htm.*
Himalayan Herbal Healthcare webpage, "C—Chyavanaprash concentrate," Internet Archive Wayback Machine, Feb. 2002, retrieved Feb. 20, 2008, http://web.archive.org/web/20020207235147/http://www.himalayahealthcare.com/aboutayurveda/cahc.htm.*
Derwent English Abstract of German Patent Application DE-4012000, Oct. 1990.*
Nagashayana, N., et al., "Association of L-Dopa with Recovery Following Ayurveda Medication in Parkinson's Disease", *Journal of the Neurological Sciences*, vol. 176, No. 2, Jun. 15, 2000, pp. 124-127.
Sohni, Y.R. et al., "Activity of a Crude Extract Formulation in Experimental Hepatic Amoebiasis and in Immunomodualtion Studies", *Journal of Ethnopharmacology*, Elsevier Scientific Publishers, Ltd., vol. 54, No. 2-3, 1996, pp. 119-124.
Nagashayana, N. et al., "Association of L-DOPA with recorvery following *Ayurveda* medication in Parkinson's disease," *Journal of the Neurological Sciences*, 2000, vol. 176, pp. 124-127.
Sohni, Y. et al., "Activity of a crude extract formulation in experimental hepatic amoebiasis and in immunomodulation studies," *Journal of Ethnopharmacology*, 1996, vol. 54, pp. 119-124.

* cited by examiner

*Primary Examiner*—Christopher R. Tate
(74) *Attorney, Agent, or Firm*—Alston & Bird LLP

(57) ABSTRACT

The invention provides a novel herbal soft drink comprising decoction of plants selected from *Sida* sps., *Vitis vinifera, Withania somnifera, Boerhaavia diffusa* and *Tinospora cordifolia* for the protection and prevention of health and in particular, but not exclusively with antioxidant, immunoenhancing, hepatoprotective, cardiotonic, diuretic, digestive, choleretic, nervine relaxant properties.

13 Claims, No Drawings

HERBAL SOFT DRINK

TECHNICAL FIELD

The present invention relates to the development of health protective herbal soft drink.

BACKGROUND ART

Diet or food therapy is emerging as the latest trend in health care programme. It is now said that there will be more dieticians than physician in the present century as many diseases can be prevented if the right kind of diet is prescribed. Herbs into our lives in an ongoing way, it is easier to modify an existing habit than to create a new one. Consumption of the right kind of food articles and drinks suited to the climate, age and constitutional, natures of the individuals are getting greater scientific security and attention. The rich and diverse traditional diet practices prevalent among various communities with the regional variations are now found to health protective/promoting. Over 1000 different kinds of alcoholic drinks, soft drinks, beverages and medicinal drinks are traditionally consumed in India. But unfortunately with the introduction of various exotic drinks many of the local drinks, which are mostly plant based, are fast disappearing and some of them almost forgotten. Acknowledging this truth The inventors undertook a critical study of many of such drink and with the modern scientific understanding of beverages have designed herbal soft drink. This drink is fortified with many health protective and promotive attributes such as hepatoprotective, anti-oxidant and immuno-enhancing, besides providing instant energy and vitality. These properties have been authenticated/validated through appropriate pharmacological investigations and clinical studies. The drink is diuretic and has cooling effect like other soft drinks of summer. The result will be a boon to consumers, in terms of herbal alternatives and availability.

Reference is made to *Bhaishjya Ratnavali/Vatvyadhiyadhikar* for "*Sida cordifolia*" as major ingredient of "*Balarishta*" with eleven other ingredients including jaggery as base for fermentation, *Elettaria cardamomum, Withania somnifera,* and *Woodfordia fruticosa,* recommended for treatment of neurogenic disorder, an ideal restorative.

The reference is made to the classical text book of Ayurveda "*Charak Samhita*" *Sutrasthan* Chapt-4 wherein *Sida* sps. is used for *Vrinhaneeya* and *Balya* properties i.e. it nourishes the body tissue and increases the body weight and acts as tonic.

The reference in made to the book *Dhanvantari Nighantoo* wherein *Sida* sps. described for *Varishyam, Balyam, Raktapittam Kshayam Hanti, Bala ojavardhyatiyapi*, which means that it is Aphrodisiac, tonic, anti-bleeding disorder, improve vitality and immunity.

The reference is made to the book "Bhav Prakash Nighantoo" wherein *Sida* sps. is considered as Bal-Kantikarit, i.e. improves vitality and lusture.

Reference is made to classical Ayurvedic text of "*Laghutrayi*"—*Sharangdhar Samhita/Madhyam Khand*/Chapt-10 for "*Vitis vinifera*", which is used as major ingredient of "*Draksharishta*" with ten minor ingredients including jaggery as base for fermentation, *Elettaria cardamomum, Cinnamomum* and *Woodfordia fruticosa,* indicated for "Urahkshat" i.e. phthisis (an advance stage of pulmonary tuberculosis)

Reference is made to U.S. Pat. No. 6,375,992 wherein a composition for hydrating mammalian skin comprises red grape extract.

Reference is made to classical text of Ayurvedic formulation—*Bhaishjya Ratanavali/Murchcha Rogadhikar* for "*Withania somnifera*", which is major ingredient of "*Aswagandharishta*" with twenty-eight other ingredients including jaggery as base for fermentation, *Elettaria cardamomum, Cinnamomum, Glycyrrhiza glabra* and *Woodfordia fruticosa*, and indicated for general debility and weakness, relieving tension and anxiety.

Reference is made of website www.globalnutrients.net/herbal_powders_information.htm wherein *Withania somnifera* is one of the most widespread tranquilizes used in India, where it hold a position of importance similar to ginseng in China. It acts mainly on the reproductive and nervous systems, having a rejuvenative effect on the body, and is used to improve vitality and aid recovery after chronic illness.

Reference is made to *Bhaishjya Ratnavali/Shoth Rogadhikar* for "*Boerhaavia diffusa*" used as major ingredient of "*Punarnavarishta*" with seventeen other ingredients including jaggery as base for fermentation, *Sida cordifolia, Tinospora cordifolia* and *Woodfordia fruticosa*, used for diuretic activity indicated in the treatment of oedema and ascites.

Reference is made to website www.drlindaberry.com/products/metagenics/mics.htm wherein herbal formulation Liv. 52™ for liver disorders contains *Phyllanthus niruri/P. amarus, Boerhaavia diffusa* and *Tinospora cordifolia* along with some other medicinal plants.

Reference is made to *Bhaishjya Ratnavali/Jwaradhikar* for "*Tinospora cordifolia*" used as major ingredient of "*Amritarishta*" with thirteen other ingredients including jaggery as base for fermentation, *Elettaria cardamomum, Cinnamomum* and *Woodfordia fruticosa*, indicated for treatment of fever and peripheral neuritis.

Reference is made to website www.herbpatch.com/herbs&7.htm wherein *Tinospora cordifolia* along with some other medicinal plants used in a formulation an Ayurvedic formulation SKN-AV, to restore the body to balanced state will being, the skin in particular.

Reference is made to U.S. Pat. No. 5,886,029 wherein a medicinal composition for treatment of diabetes comprises *Tinospora cordifolia* and *cinnamomum tamala* along with some other ingredients.

Reference is made to U.S. Pat. No. 6,136,316 wherein a hepatoprotective composition for treating acute hepatitis B and E virus infection comprises *Phyllanthus amarus, Tinospora cordifoia* and *Boerhavia diffusa.*

Reference is made to U.S. Pat. No. 5,693,327 for the treatment of skin disorders at least one wherein a herbal composition for the treatment of skin disorders comprises of at least one plant from *Tinospora cordifolia, Glycyrrhiza glabra* and *Phyllanthus emblica* along with some other listed plants An Ayurvedic composition for the prophylaxis and treatment of AIDS, flu, TB, hepatitis and other immuno-deficiancies comprises of *Tinospora cordifolia, Phyllanthus nirurii, phyllanthus emblica* along with some other plant ingredients.

Reference is made to U.S. Pat. No. 5,683,698 wherein a formulation for alleviating symptoms associated with arthritis comprises of *Tinospora cordifolia* and *Withania somnifera* along with some other ingredients.

Reference is made to U.S. Pat. No. 6,153,198 wherein an alcoholic extract *Withania somnifera* produces a cognition effect and learning facility for the user.

Reference is made to U.S. Pat. No. 5,494,668 wherein a composition for treating musculoskeletal disease such as rheumatoid arthritis and osteoarthritis comprises of extracts of *Aswagandha-withania somnifera* along with some other plant material extracts.

Reference is made to website www.holistichealthplus.com/HT/hepatitis.htm wherein herbs with powerful liver protective properties, adding in detoxification and promoting bile production and flow, as well as nourishing and repairing liver tissue.

OBJECTS OF THE INVENTION

The primary objective of the invention is to invent an immuno-enhancing, anti-oxidant, hepatoprotective, anti-fatigue, anti-stress herbal soft drink.

Another objective of the invention is that the herbal health drink gives instant energy and combat fatigue.

Yet another objective of the present invention is to produce the herbal health drink with some commonly available Indian medicinal herb.

Still another objective of the invention is that the herbal health drink possesses all the advantages of soft drink and none of its disadvantages.

Another objective of the present invention is the development of jaggery based herbal soft drink having, powerful antioxidant, immunomodulator, hepatoprotective and diuretic properties.

SUMMARY OF THE INVENTION

The invention provides a novel herbal soft drink comprising decoction of plants selected from *Sida* sps., *Vitis vinifera, Withania somnifera, Boerhaavia diffusa* and *Tinospora cordifolia* for the protection and prevention of health and in particular, but not exclusively with antioxidant, immunoenhancing, hepatoprotective, cardiotonic, diuretic, digestive, choleretic, nervine relaxant properties.

DETAILED DESCRIPTION OF THE INVENTION

The present invention provides a herbal soft drink comprising of: a concentrated herbal extract obtained from a mixture of herbs selected from *Sida* sps., *Boerhaavia diffusa, Vitis vinifera, Tinospora cordifolia* and *Withania somnifera* along with jaggery, a fermenting agent and carbonated water.

In an embodiment of the present invention, the percentage ratio of *Sida* sps.: *Boerhaavia diffusa: Vitis vinifera: Tinospora cordifolia: Withania somnifera* in the powdered mixture is in the range of 15 to 20:5 to 10:15 to 20:5 to 10:5 to 10.

In another embodiment of the present invention, the w/w ratio of the jaggery: concentrated herbal extract is in the range of 1:3 to 1:4.

In yet another embodiment of the present invention, the fermenting agent used is *Sacromyces* strain and flowers of *Woodfordia fructose.*

In still another embodiment of the present invention, the percentage ratio of fermenting agent added is in the range of 4 to 16.

In one more embodiment of the present invention, the w/w ratio of carbonated water: the mixture of the concentrated extract, jaggery and the fermenting agent is in the range of 1:3 to 1:5.

In one another embodiment of the present invention, the soft drink provides antioxidant, hepatoprotective, cardiotonic, diuretic, digestive, choleretic, nervine relaxant and immuno-enhancing properties.

In a further embodiment of the present invention, total solids content in the soft drink ranges from 30-40%.

The present invention also provides a process for preparing the herbal soft drink having antioxidant, hepatoprotective, cardio-tonic, diuretic, digestive, choleretic, nervine relaxant and immuno-enhancing properties, the said process comprising the steps of:

(a) obtaining plant parts of *Phyllanthus* sps., *Glycyrrhiza glabra, Boerhaavia diffusa, Vitis vinifera, Tinospora cordifolia* and *Withania somnifera;*
(b) crushing the plant parts and mixing them to obtain a powdered mixture;
(c) adding water to the powdered mixture of step (b) to obtain an aqueous extract;
(d) concentrating the aqueous extract of step (c);
(e) filtering the concentrated extract of step (d);
(f) mixing jaggery to the filtered extract of step (e);
(g) adding *Sacromyces* strain and a fermenting agents to the mixture of step (f);
(h) fermenting the mixture of step (g) for a time period ranging between 3 to 6 days;
(i) filtering the fermented mixture of step (h);
(j) concentrating the fermented filtrate of step (i) to obtain a stock solution, and
(k) mixing the stock solution of step (j) with carbonated water in the w/w ratio of 1:3 to 1:5 to obtain the herbal soft drink.

In an embodiment of the present invention, the plant parts used are selected from the group consisting of leaf, stem, root, fruits and whole plant.

In another embodiment of the present invention wherein in step (b), the percentage ratio of *Sida* sps.: *Boerhaavia diffusa: Vitis vinifera: Tinospora cordifolia: Withania somnifera* in the powdered mixture is in the range of 15 to 20:5 to 10:15 to 20:5 to 10:5 to 10.

In yet another embodiment of the present invention wherein in step (c), the w/w ratio of water added to the powdered mixture is in the range of 5:1 to 10:1.

In still another embodiment of the present invention wherein in step (d), the aqueous extract is concentrated to 1/3 to 1/4 of its original volume.

In one more embodiment of the present invention wherein in step (f), the w/w ratio of the jaggery: filtered extract is in the range of 1:3 to 1:4.

In one another embodiment of the present invention wherein in step (g), the fermenting agent used is selected from Sacromyces strain and flowers of *Woodfordia fructose.*

In a further embodiment of the present invention wherein in step (j), the fermented filtrate is concentrated to 4/5 to 1/5 of its original volume.

In an embodiment of the present invention, there is provided a herbal soft drink for quenching thirst and cooling effect.

In another embodiment of the present invention there is provided herbal soft drink the composition further comprises *Phyllanthus* sps. *Glycyrrhiza glabra* for hepatoprotective activity.

In yet another embodiment of the present invention, there is provided herbal soft drink the composition comprises *Glycyrrhiza glabra* for improving gastro-intestinal conditions under stress.

In still another embodiment of the present invention, there is provided herbal soft drink the composition is comprises *Cinnamomum* sps. to improve aroma.

In one more embodiment of the present invention, plants used have anti-oxidant property.

In one another embodiment of the present invention, plants used have hepatoprotective property.

In an embodiment of the present invention, plants used have anxiolytic property.

In another embodiment of the present invention, plants used have no cardiovascular toxicity.

In still another embodiment of the present invention, plants used have diuretic property.

In yet another embodiment of the present invention, plants used are non-toxic.

BRIEF DESCRIPTION OF THE TABLES

Table 1: provides the SOD activity in brain of animals treated with herbal preparations C1 and C2 (n=5).

Table 2: Rate of TBARS formation in brain of rats treated with herbal praperations C1 and C2 (n=5).

Table 3: Level of TBARS formation after in vitro supplementation of C1 and C2 to rat brain homogenate.

Table 4: SOD mimetic activity in vitro in the herbal preparations C1 and C2.

Table 5: The table illustrates some of the properties found to be associated with the plant used in the present invention.

EXAMPLE-1

| | |
|---|---|
| *Sida* sps. | 15% |
| *Boerhaavia diffusa* | 10% |
| *Vitis vinifera* | 15% |
| *Tinospora cordifolia* | 5% |
| *Withania somnifera* | 5% |
| *Woodfordia fruticosa* | 5% |
| Jaggery | 34% |
| Water | q. s. to make 100 ml decoction |

EXAMPLE-2

| | |
|---|---|
| *Sida* sps. | 18% |
| *Boerhaavia diffusa* | 8% |
| *Vitis vinifera* | 20% |
| *Tinospora cordifolia* | 5% |
| *Withania somnifera* | 10% |
| *Woodfordia fruticosa* | 5% |
| Jaggery | 30% |
| Water | q. s. to make 100 ml decoction |

EXAMPLE-3

| | |
|---|---|
| *Sida* sps. | 20% |
| *Boerhaavia diffusa* | 5% |
| *Vitis vinifera* | 15% |
| *Tinospora cordifolia* | 6% |
| *Withania somnifera* | 5% |
| *Woodfordia fruticosa* | 5% |
| Jaggery | 40% |
| Water | q. s. to make 100 ml decoction |

EXAMPLE-4

| | |
|---|---|
| *Sida* sps. | 18% |
| *Boerhaavia diffusa* | 10% |
| *Vitis vinifera* | 20% |
| *Tinospora cordifolia* | 6% |
| *Withania somnifera* | 7% |
| *Woodfordia fruticosa* | 10% |
| Jaggery | 35% |
| Water | q. s. to make 100 ml decoction |

EXAMPLE-5

| | |
|---|---|
| *Sida* sps. | 20% |
| *Boerhaavia diffusa* | 10% |
| *Vitis vinifera* | 20% |
| *Tinospora cordifolia* | 5% |
| *Withania somnifera* | 5% |
| *Woodfordia fruticosa* | 5% |
| Jaggery | 30% |
| Water | q. s. to make 100 ml decoction |

EXAMPLE-6

| | |
|---|---|
| *Sida* sps. | 18% |
| *Boerhaavia diffusa* | 10% |
| *Vitis vinifera* | 20% |
| *Tinospora cordifolia* | 5% |
| *Withania somnifera* | 5% |
| *Woodfordia fruticosa* | 10% |
| Jaggery | 30% |
| Water | q. s. to make 100 ml decoction |

EXAMPLE-7

| | |
|---|---|
| *Sida* sps. | 15% |
| *Boerhaavia diffusa* | 5% |
| *Vitis vinifera* | 15% |
| *Tinospora cordifolia* | 5% |
| *Withania somnifera* | 5% |
| *Woodfordia fruticosa* | 5% |
| Jaggery | 30% |
| Water | q. s. to make 100 ml decoction |

EXAMPLE-8

| | |
|---|---|
| *Sida* sps. | 15% |
| *Boerhaavia diffusa* | 5% |
| *Vitis vinifera* | 20% |
| *Tinospora cordifolia* | 8% |
| *Withania somnifera* | 8% |
| *Woodfordia fruticosa* | 8% |
| Jaggery | 30% |
| Water | q. s. to make 100 ml decoction |

TABLE 1

SOD activity in brain of animals treated with herbal preparations C1 and C2 (n = 5)

| Type of treatment | Treatment group | Parameter studied | | |
|---|---|---|---|---|
| | | SOD activity units/ml | Protein mg/ml | Specific activity Units/mg protein |
| 7 days oral treatment | Control | 8.46 ± 0.67 | 3.39 ± 0.26 | 2.49 ± 0.23 |
| | C1 | 6.50 ± 0.70 | 3.14 ± 0.10 | 2.05 ± 0.19 |
| 30 days oral treatment | Control | 9.52 ± 0.95 | 3.56 ± 0.33 | 2.65 ± 0.59 |
| | C1 | 6.89 ± 1.4 | 4.65 ± 0.39 | 1.50 ± 0.42 |

TABLE 2

Rate of TBARS formation in brain of rats treated with herbal preparations C1 and C2 (n = 5)

| Type of treatment | Treatment group | Parameter studied | | |
|---|---|---|---|---|
| | | nm MDA/mg protein at 0 minutes | nm MDA/mg protein at 60 minutes | Rate of MDA formation nM MDA/mg protein/hr |
| 7 days oral treatment | Control | 1.35 ± 0.46 | 2.50 ± 0.55 | 1.26 ± 0.14 |
| | C1 | 1.70 ± 0.39 | 3.03 ± 0.49 | 1.33 ± 0.11 |
| 30 days oral treatment | Control | 2.08 ± 1.18 | 2.43 ± 1.19 | 0.435 ± 0.11 |
| | C1 | 1.27 ± 0.07 | 1.84 ± 0.23 | 0.44 ± 0.14 |

TABLE 3

Level of TBARS formation after invitro supplementation of C1 and C2 to rat brain homopgenate

| S. NO | Supplementation to basal system. | nM MDA/mg protein at 0 minutes | nM MDA/mg protein at 60 minutes | Rate of MDA formation |
|---|---|---|---|---|
| 1. | Control 1 | 0.988 | 2.071 | 1.083 |
| 3. | 50 µl C1 | 1.142 | 1.193 | 0.051 |
| 4. | 100 µl C1 | 1.389 | 1.346 | Nil(−0.04) |

TABLE 4

SOD mimetic activity in vitro in the herbal preparations C1 and C2

| S. No | Sample | SOD mimetic activity units/ml |
|---|---|---|
| 1. | C1 | 22.69 |

CONCLUSION

Herbal preparation showed SOD Mimetic activity in vitro and radical quenching capacity as can be seen from no change in MDA levels in the presence of this preparation. In vitro also this preparation was found to have antioxidant potential.

Note: SOD: Super oxide dismutase; TBARS: Thiobarbituric reactive substances and MDA: Malondialdehyde

TABLE 5

The table illustrates some of the properties found to be associated with the plant used in the present invention

| S. No. | Plant name (Vernacular name) | Family | Chemical constituents | Properties |
|---|---|---|---|---|
| 1. | *Sida* spp. (Bala) | *Malvaceae* | Alkaloids, ephedrine, fatty oil, seroids, phytosterol, resin, recin acid, potassium nitrate and mucin. | Demulcent, laxative, as refrigerant in fever, used against dysentery, for poulticing ulcers, emollient, diuretic, astringent, tonic, given in urinary diseases, bilious disorders and gonorrhoea, used in cystitis, strangury, haematuria and in nervous disorders. |
| 2. | *Boerhaavia diffusa* (Punarnava) | *Nyctaginaceae* | Quinolizidine alkaloids, punarnavine 1 & 2, fatty oil, potassium salts, hypoxanthine-9-L- | Diuretic, anti-inflammatory, for treatment of |

TABLE 5-continued

The table illustrates some of the properties found to be associated with the plant used in the present invention

| S. No. | Plant name (Vernacular name) | Family | Chemical constituents | Properties |
|---|---|---|---|---|
| | | | arabinofuranoside, oxalates, myricyl alcohol, myristic acid, D-glucose, a polysaccharide and punarnavoside, | inflammatory renal diseases like nephrotic syndrome, oedema and ascites resulting from cirrhosis of the liver and chronic peritonitis, efficacious in abdominal tumors and cancer, antibacterial, cardiotonic. |
| 3. | *Vitis vinifera* (Draksha) | *Vitaceae* | Leucoanthocyanins, sugars, acids and phenolics, iron, bromide, iodide and fluoride, vitamins, carotene, thiamine, riboflavin, niacin, vitamin C, pyridoxine, pantothenic acid, folic acid, biotin, inositol, bioflavinoids, carbohydrate, amino acids. tartaric and malic acids. | Stomachic, diuretic, demulcent and cooling, laxative, and expectorant. |
| 4. | *Tinospora cordifolia* (Giloe) | *Menispermaceae* | Glucoside, alkaloidal constituents (including berberine), bitter glucoside giloin, giloinin, gilosterol, tinosporon, tinosporic acid and tinosporol, starch, calcium, phosphorus. | Antiperiodic, antispasmodic, anti-inflammatory and antipyretic, for gout, as liniment in erysipelas, ulcers, as tonic, in the treatment of jaundice, rheumatism and leprosy, has favorable effect on endogenous insulin secretion, glucose uptake and inhibition of peripheral glucose release, |
| 5. | *Withania somnifera* (Asawagandha) | *Solanaceae* | Maltose, steroidal lactones-withanolides,, withaferin A, withanone, cuscohygrine, anahygrine, tropine, pseudotropine, anaferine, isopelletierine, 3-tropyltigloate, nicotine, withasomine, visamine, | Hypotensive, bradycardiac, respiratory-stimulating action, relaxant and antispasmodic effects against several spasmogens on intestinal, uterine, bronchial, treacheal and blood-vascular muscles. inflammatory conditions, ulcers and scabies. |

ADVANTAGES OF THE PRESENT INVENTION

1. Soft drink is purely herbal.
2. Soft drink for the protection and prevention of health and in particular, but not exclusively with antioxidant, immunoenhancing, hepatoprotective, cardiotonic, diuretic, digestive, choleretic, nervine relaxant properties.
3. Soft drink gives instant energy and combat fatigue.
4. The soft drink comprising two or more plants decoction selected from *Sida* sps., *Vitis vinifera*, *Withania somnifera*, *Boerhaavia diffusa* and *Tinospora cordifolia*.
5. Soft drink developed is non-toxic.
6. No chemical preservative or colourants are used in this soft drink.
7. Soft drink is a good source of iron.

The invention claimed is:

1. An herbal soft drink comprising a concentrated herbal extract obtained from a mixture of herbs comprising *Sida* spp., *Boerhaavia diffusa*, *Vitis vinifera*, *Tinospora cordifolia* and *Withania somnifera*, wherein the herbal soft drink further comprises jaggery, a fermenting agent and carbonated water; and wherein the percentage ratio of *Sida* spp.: *Boerhaavia diffusa: Vitis vinifera: Tinospora cordifolia: Withania somnifera* in the herbal soft drink is in the range of 15 to 20:5 to 10:15 to 20:5 to 10:5 to 10 jaggery, a fermenting agent and carbonated water.

2. The herbal soft drink as claimed in claim 1, wherein the w/w ratio of the jaggery: concentrated herbal extract is in the range of 1:3 to 1:4.

3. The herbal soft drink as claimed in claim 1, wherein the fermenting agent used is *Saccharomyces* strain and flowers of *Woodfordia fruticosa*.

4. The herbal soft drink as claimed in claim 3, wherein the percentage ratio of fermenting agent in the herbal soft drink is in the range of 4 to 16.

5. The herbal soft drink as claimed in claim 1, wherein the w/w ratio of carbonated water: the mixture of the concentrated extract, jaggery, and the fermenting agent is in the range of 1:3 to 1:5.

6. The herbal soft drink as claimed in claim 1, wherein total solids content in the soft drink ranges from 30-40%.

7. A process for preparing the herbal soft drink of claim 1, said process comprising the steps of:

(a) obtaining plant parts from herbs comprising *Sida* spp., *Boerhaavia diffusa, Vitis vinifera, Tinospora cordifolia* and *Withania somnifera;*
(b) crushing the plant parts and mixing them to obtain a powdered mixture;
(c) adding water to the powdered mixture of step (b) to obtain an aqueous extract;
(d) concentrating the aqueous extract of step (c);
(e) filtering the concentrated extract of step (d);
(f) mixing jaggery to the filtered extract of step (e);
(g) adding a fermenting agent to the mixture of step (f);
(h) fermenting the mixture of step (g) for a time period ranging between 3 to 6 days;
(i) filtering the fermented mixture of step (h);
(j) concentrating the fermented filtrate of step (i) to obtain a stock solution, and
(k) mixing the stock solution of step (j) with carbonated water in the w/w ratio of 1:3 to 1:5 to obtain the herbal soft drink; wherein in step (b), the percentage ratio of *Sida* spp.: *Boerhaavia diffusa: Vitis vinifera: Tinospora cordifolia: Withania somnifera* in the herbal soft drink is in the range of 15 to 20:5 to 10:15 to 20:5 to 10:5 to 10.

8. The process claimed in claim 7, wherein the plant parts used are selected from the group consisting of leaf, stem, root, and fruits.

9. The process claimed in claim 7 wherein in step (c), the w/w ratio of water added to the powdered mixture is in the range of 5:1 to 10:1.

10. The process claimed in claim 7 wherein in step (d), the aqueous extract is concentrated to 1/3 to 1/4 of its original volume.

11. The process claimed in claim 7 wherein in step (f), the w/w ratio of the jaggery: filtered extract is in the range of 1:3 to 1:4.

12. The process claimed in claim 7 wherein in step (g), the fermenting agent used is selected from *Saccharomyces* strain and flowers of *Woodfordia fruticosa.*

13. The process claimed in claim 7 wherein in step (j), the fermented filtrate is concentrated to 4/5 to 1/5 of its original volume.

* * * * *